United States Patent
Ziv-Ari et al.

(10) Patent No.: US 12,226,258 B2
(45) Date of Patent: Feb. 18, 2025

(54) SYSTEMS AND METHODS FOR TRACKING AN ANATOMICAL FOCAL POINT

(71) Applicant: BIOSENSE WEBSTER (ISRAEL) LTD., Yokneam (IL)

(72) Inventors: Morris Ziv-Ari, Atlit (IL); Assaf Cohen, Kiryat Bialik (IL); Lior Zar, Poria Illit (IL); Nadav Barnea, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 48 days.

(21) Appl. No.: 17/963,501

(22) Filed: Oct. 11, 2022

(65) Prior Publication Data

US 2024/0115239 A1    Apr. 11, 2024

(51) Int. Cl.
*A61B 6/00* (2024.01)
*A61B 5/339* (2021.01)
(Continued)

(52) U.S. Cl.
CPC .............. *A61B 8/463* (2013.01); *A61B 5/339* (2021.01); *A61B 5/367* (2021.01); *A61B 8/0883* (2013.01);
(Continued)

(58) Field of Classification Search
CPC ....... A61B 5/339; A61B 5/367; A61B 8/0883; A61B 8/12; A61B 8/4254; A61B 8/4416; A61B 8/5223
See application file for complete search history.

(56) References Cited

U.S. PATENT DOCUMENTS 5,391,199 A    2/1995    Ben
5,443,489 A    8/1995    Ben
(Continued)

FOREIGN PATENT DOCUMENTS

WO    WO202203993 A1    2/2022

OTHER PUBLICATIONS

Bohs, Laurence N., and Gregg E. Trahey, "A novel method for angle independent ultrasonic imaging of blood flow and tissue motion," IEEE Transactions on biomedical engineering 38.3 (1991): 280-286.
(Continued)

*Primary Examiner* — Joel F Brutus

(57) ABSTRACT

A method includes obtaining an electroanatomical map, which maps a portion of a heart while the heart experiences an arrhythmia, obtaining a sequence of images of the heart acquired by an ultrasonic probe, the sequence including one or more arrhythmic images acquired while the heart experiences the arrhythmia and one or more rhythmic images acquired while the heart is in sinus rhythm, the ultrasonic probe including a sensor that outputs, during the acquisition of the sequence of images, a signal indicating a location and an orientation of the probe in a coordinate system of the electroanatomical map, based on the signal, identifying, in one of the arrhythmic images, an anatomical portion represented by a particular portion of the electroanatomical map, by tracking the anatomical portion through the sequence of images, identifying the anatomical portion in at least one of the rhythmic images, and displaying an output in response thereto.

20 Claims, 4 Drawing Sheets

(51) Int. Cl.
*A61B 5/367* (2021.01)
*A61B 8/00* (2006.01)
*A61B 8/08* (2006.01)
*A61B 8/12* (2006.01)
*G06T 7/73* (2017.01)

(52) U.S. Cl.
CPC .............. *A61B 8/12* (2013.01); *A61B 8/4254* (2013.01); *A61B 8/4416* (2013.01); *A61B 8/5223* (2013.01); *G06T 7/74* (2017.01); *G06T 2207/10016* (2013.01); *G06T 2207/10132* (2013.01); *G06T 2207/30048* (2013.01)

(56) References Cited

U.S. PATENT DOCUMENTS

| | | | |
|---|---|---|---|
| 5,558,091 | A | 9/1996 | Acker |
| 5,944,022 | A | 8/1999 | Nardella |
| 5,983,126 | A | 11/1999 | Wittkampf |
| 6,177,792 | B1 | 1/2001 | Govari |
| 6,690,963 | B2 | 2/2004 | Ben |
| 6,788,967 | B2 | 9/2004 | Ben |
| 7,536,218 | B2 | 5/2009 | Govari |
| 8,456,182 | B2 | 6/2013 | Bar-Tal |
| 2016/0249880 | A1* | 9/2016 | Konofagou ............ G16H 50/30 600/438 |
| 2017/0018313 | A1 | 7/2017 | Chmiel et al. |
| 2018/0342072 | A1* | 11/2018 | Raudins .................. G06T 7/292 |

OTHER PUBLICATIONS

International Search Report for Corresponding PCT Appln. No. PCT/IB2023/060015 dated Feb. 6, 2024.

D. L. Packer et al: "New generation of electro-anatomic mapping: full intracardiac ultrasound image integration", Europace, vol. 10, No. Supplement 3, Nov. 1, 2008 (Nov. 1, 2008), pp. iii35-iii41.

Proietti Riccardo et al: "Intracardiac echo-facilitated 3D electroanatomical mapping of ventricular arrhythmias from the papillary muscles: assessing the 'fourth dimension' during ablation", Europace, Aug. 2, 2016 (Aug. 2, 2016), p. euw099.

* cited by examiner

SYSTEMS AND METHODS FOR TRACKING AN ANATOMICAL FOCAL POINT

FIELD OF THE DISCLOSURE

The present disclosure is related generally to the field of electrophysiology, and specifically to the treatment of cardiac arrhythmias.

BACKGROUND

Co-assigned U.S. Pat. No. 11,147,497 to Ziv-Ari et al. describes a method including receiving sets of signals during multiple cardiac cycles, each set indicating, for a probe inserted into a cardiac chamber, a 3D location of a distal end of the probe, electrical potentials measured at the location, and respective times during a given cycle when the potentials were measured. The received measurements and the respective times are compared to a first template for a sinus rhythm cycle and a second template for a non-sinus rhythm cycle so as to identify a sequence of cycles including consecutive first, second, and third cycles wherein the first and second cycles match the first template and the third cycle matches the second template. A physical map is generated based on the locations. Based on the received locations and corresponding potentials, an electroanatomic map including the local activation times for the non-sinus rhythm cycle overlaid on the physical map is rendered to a display.

BRIEF DESCRIPTION OF THE DRAWINGS

The present disclosure will be more fully understood from the following detailed description of examples thereof, taken together with the drawings, in which.

DETAILED DESCRIPTION OF EXAMPLES

Overview

Figure 1:
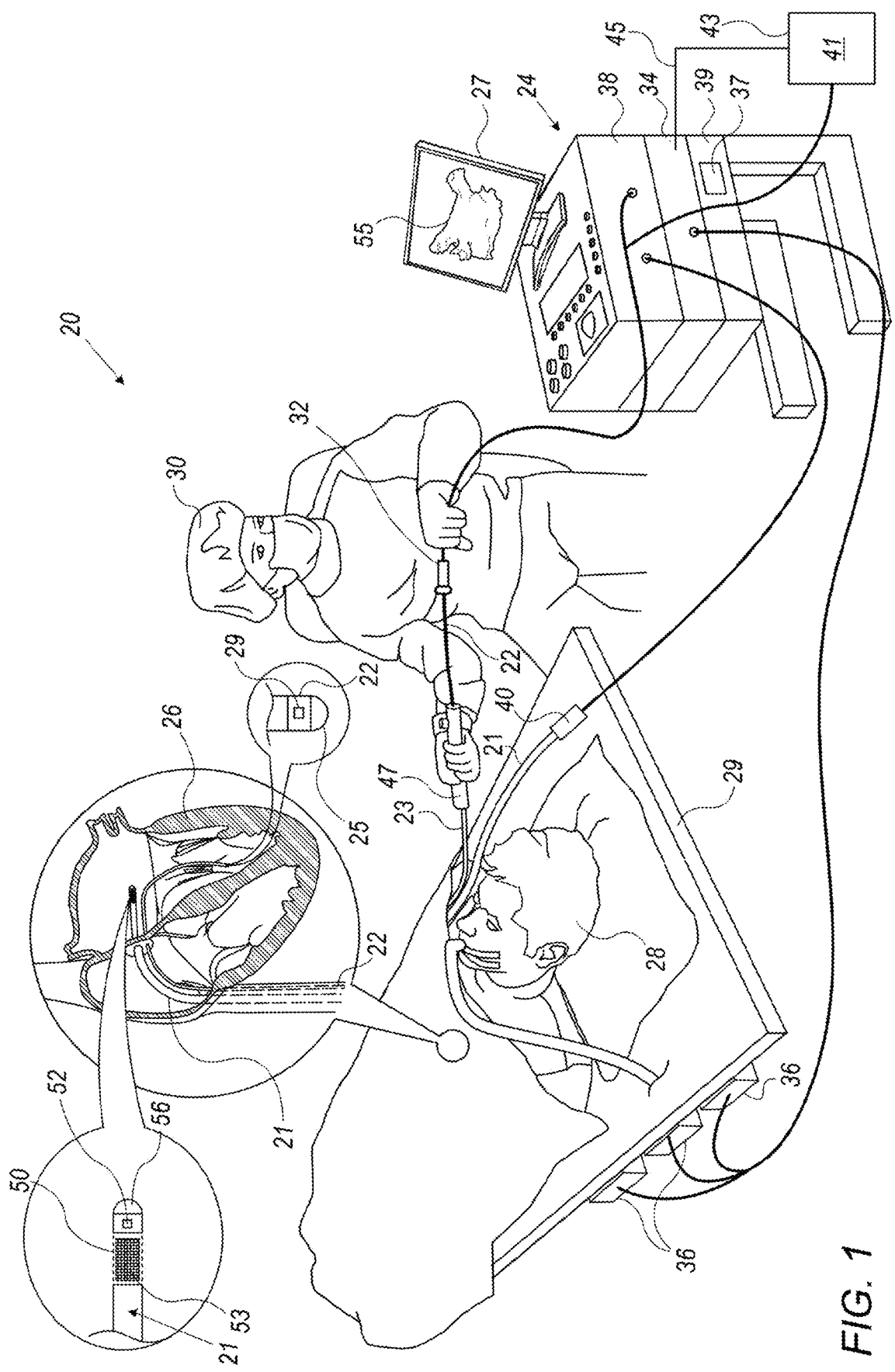
FIG. 1 is a schematic illustration of a mapping-and-ablation system, in accordance with some examples of the present disclosure.

Ablation of a focal point of a cardiac arrhythmia, such as premature ventricular contraction (PVC), is often performed while the heart is in sinus rhythm. In such cases, it may be helpful to display, during the ablation procedure, a "rhythmic" map representing the relevant anatomy during sinus rhythm and annotated so as to indicate the location of the focal point. However, to find the focal point, the physician needs to see the electrical activity of the heart during the arrhythmia, which a "rhythmic" map does not show.

One solution to this challenge is to construct a hybrid electroanatomical map, which includes a rhythmic anatomical map annotated so as to show the electrical properties of the heart during the arrhythmia. Subsequently to constructing the hybrid map, the physician may mark the focal point on the hybrid map, and then refer to the hybrid map during the procedure. However, a potential problem with this approach is that the arrhythmic electrical properties may not be mapped correctly to the rhythmic anatomy, due to differences in morphology between the rhythmic and arrhythmic states.

Hence, the present disclosure provides an alternate solution to the aforementioned challenge. Per this solution, a rhythmic electroanatomical map and an arrhythmic electroanatomical map are constructed, using data acquired by a mapping probe. In addition, a sequence of ultrasound images showing the area of the focal point is acquired, by an ultrasound probe, while the heart transitions from sinus rhythm to an episode of arrhythmia or vice versa. The mapping probe and ultrasound probe are tracked by the same tracking system, such that the ultrasound images are registered to each of the maps.

First, the physician marks the focal point on the arrhythmic electroanatomical map. Using the registration of the map to the ultrasound images, a processor locates the focal point in one of the "arrhythmic images," i.e., one of the images acquired during the episode of arrhythmia. Subsequently, the processor tracks the focal point forward or backward through the sequence, until reaching one of the "rhythmic images," i.e., one of the images acquired during sinus rhythm. (Typically, both the starting arrhythmic image and ending rhythmic image were acquired at the same phase in the cardiac cycle, this phase being represented by both maps.) Subsequently, using the registration, the processor marks the focal point on the rhythmic map. The physician may then refer to the rhythmic map so as to locate the focal point during the procedure.

In other examples, the processor constructs a more accurate hybrid electroanatomical map, relative to conventional techniques. Optionally, a focal point or any other point of interest may then be marked on the hybrid map.

To construct the hybrid map, the processor first selects multiple representative portions of the arrhythmic map. For each of the representative portions, the processor uses the ultrasound-based technique described above to locate the corresponding portion of a rhythmic anatomical map, which represents the relevant anatomy during sinus rhythm. The processor then associates the value an electrical property, which is associated with the representative portion of the arrhythmic map, with the corresponding portion of the rhythmic anatomical map. After performing any required interpolation of the values over the rhythmic map, the processor annotates the rhythmic map so as to indicate the values.

System Description

Reference is initially made to FIG. 1, which is a schematic illustration of a mapping-and-ablation system 20, in accordance with some examples of the present disclosure.

System 20 comprises a mapping-and-ablation probe 22, which is proximally connected to a mapping console 24. Probe 22 comprises one or more electrodes 25 at its distal end. Electrodes 25 are configured to acquire intracardiac signals from the tissue of a heart 26 of a subject 28 and to apply ablating signals to the tissue. Probe 22 further comprises, at its distal end, a tracking sensor 29 configured to output a signal indicative of a position and orientation of sensor 29. The probe may be controlled using a control handle 32.

Probe 22 is inserted by a physician 30 into a chamber, such as the left ventricle, of heart 26, e.g., via the superior vena cava of subject 28. Typically, the probe is inserted through a sheath 23, the proximal end of which may be connected to a handle 47. Subsequently to inserting probe 22 into the chamber of the heart, the physician moves the distal end of the probe along the tissue of the chamber while electrodes 25 acquire intracardiac signals from the tissue.

System 20 further comprises a mapping processor 39, which is typically contained in mapping console 24. Based on the signal from sensor 29, mapping processor 39 calculates the location, in heart 26, at which each of the intracardiac signals was acquired. Based on the signals and location information, the processor constructs an electroanatomical map 55 of the tissue.

System 20 further comprises an ultrasound (US) probe 21 proximally connected to mapping console 24 and to an ultrasound console 43. US probe 21 comprises, at its distal end, a two-dimensional (e.g., 32×64) array 50 of ultrasound transducers 53, and a tracking sensor 52. Sensor 52 is configured to output a signal indicative of a position and orientation of the sensor. US probe 21 may be controlled using a control handle 40.

System 20 further comprises an ultrasound processor 41, which is typically contained in ultrasound console 43. Based on signals output by transducers 53, processor 41 constructs ultrasound images, which are typically three dimensional.

Mapping processor 39 and ultrasound processor 41 are configured to exchange communication with one another over any suitable wireless or wired communication medium 45. For example, ultrasound processor 41 may communicate each of the ultrasound images to mapping processor 39. Based on the signal from sensor 52 and a predefined registration of the sensor to array 50, mapping processor 39 may calculate the location and orientation of the anatomy represented in each of the ultrasound images.

System 20 further comprises a memory 37, which may comprise any suitable type of volatile memory, such as random access memory (RAM), and/or non-volatile memory, such as flash memory. Memory 37 may be accessed by mapping processor 39 and/or ultrasound processor 41. Memory 37 may store the ultrasound images and/or any other data.

Physician 30 inserts US probe 21 into heart 26, e.g., via the superior vena cava of subject 28. Subsequently, the physician uses US probe 21 to acquire ultrasound images of the anatomy that is mapped using mapping-and-ablation probe 22. Contours shown in at least some of these images may be marked manually (e.g., by physician 30) or automatically (e.g., by mapping processor 39), and the marked images may then supplement the anatomical data used for constructing map 55. Alternatively or additionally, as further described below with reference to FIG. 3, at least some of the images may be used to track a focal point of an arrhythmia and/or other portions of the subject's anatomy.

In some examples, system 20 comprises one or more magnetic-field generators 36 configured to generate a magnetic field in the vicinity of subject 28, and each of the tracking sensors comprises one or more coils. Based on the signals induced in the coils by the magnetic field, mapping processor 39 tracks the location and orientation of each of the probes. Such tracking techniques are disclosed, for example, in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

In other examples, each of the tracking sensors comprises one or more probe electrodes, and the processor tracks each of the probes based on a current or voltage distribution between the probe electrodes and reference electrodes coupled to the subject's body. Such techniques may utilize a location map calibrated, in advance, using electromagnetic sensors, as described, for example, in U.S. Pat. No. 7,536,218 to Govari et al. and U.S. Pat. No. 8,456,182 to Bar-Tal et al., whose respective disclosures are incorporated herein by reference. Alternatively, the processor may pass electric currents between the reference electrodes and measure the resulting voltages at the probe electrodes, as described, for example, in U.S. Pat. No. 5,983,126 to Wittkampf and U.S. Pat. No. 5,944,022 to Nardella, whose respective disclosures are incorporated herein by reference.

In some examples, US probe 21 and mapping-and-ablation probe 22 are situated simultaneously in the subject's heart. As a specific example, probe 22 may map the left ventricle of heart 26 while the US probe images the left ventricle from the left atrium of the heart. In other examples, one of the probes is inserted into the heart only after the other probe is withdrawn.

In some examples, US probe 21 comprises at least one electrode 56, with which the US probe performs some or all of the functionality of mapping-and-ablation probe 22. Provided the US probe performs all of the functionality of probe 22, probe 22 may be omitted from system 20.)

In yet other examples, system 20 comprises three probes: US probe 21, another probe for mapping, and another probe for ablation. System 20 further comprises electrocardiogram (ECG) electrodes (not shown) coupled to the body of subject 28 and connected to console 24. Based on the signals from the ECG electrodes, mapping processor 39 ascertains the respective phases in the ECG cycle at which the intracardiac signals and ultrasound images are acquired. Furthermore, based on the ECG signals, the mapping processor may ascertain whether the heart is in sinus rhythm or is experiencing an arrhythmia.

System 20 further comprises circuitry 38, which is typically disposed in console 24. Circuitry 38 may comprise interface circuitry configured to interface between mapping processor 39 and each of the probes. For example, the interface circuitry may digitize intracardiac signals received from the distal end of mapping-and-ablation probe 22 and pass the digitized signals to mapping processor 39. Alternatively or additionally, circuitry 38 may comprise generator circuitry configured to generate ablating signals and transmit these signals to the distal end of probe 22.

In some examples, system 20 further comprises driver circuitry 34, which is typically disposed in console 24 and is configured to drive magnetic-field generators 36.

Typically, system 20 further comprises a display 27, on which mapping processor 39 may display electroanatomical map 55, one or more ultrasound images, and/or any other suitable output.

In some examples, US probe 21 acquires transthoracic or transesophageal ultrasound images, rather than intracardiac images.

Although the present description generally assumes that mapping processor 39 carries out the processes described herein, it is noted that any one or more processors may cooperatively carry out any one of these processes. For example, ultrasound processor 41 may carry out any one of these processes alone or cooperatively with mapping processor 39. As a specific example, ultrasound processor 41 may execute the tracking functionality described herein, and communicate the output of the tracking to mapping processor 39.

In general, each of the processors described herein may be embodied as a single processor, or as a cooperatively networked or clustered set of processors. The functionality of the processor may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, the processor may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Locating a Focal Point in a Rhythmic Electroanatomical Map

Figure 2:
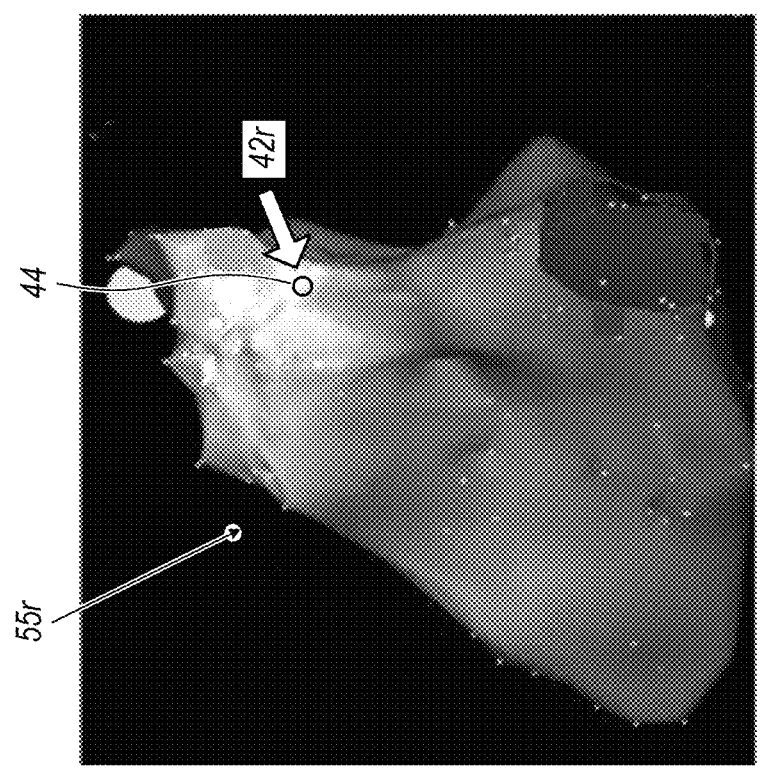
FIG. 2 is a schematic illustration of two electroanatomical maps, in accordance with some examples of the present disclosure.
Figure 2:
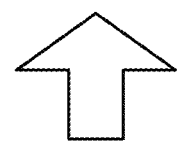
Figure 2:
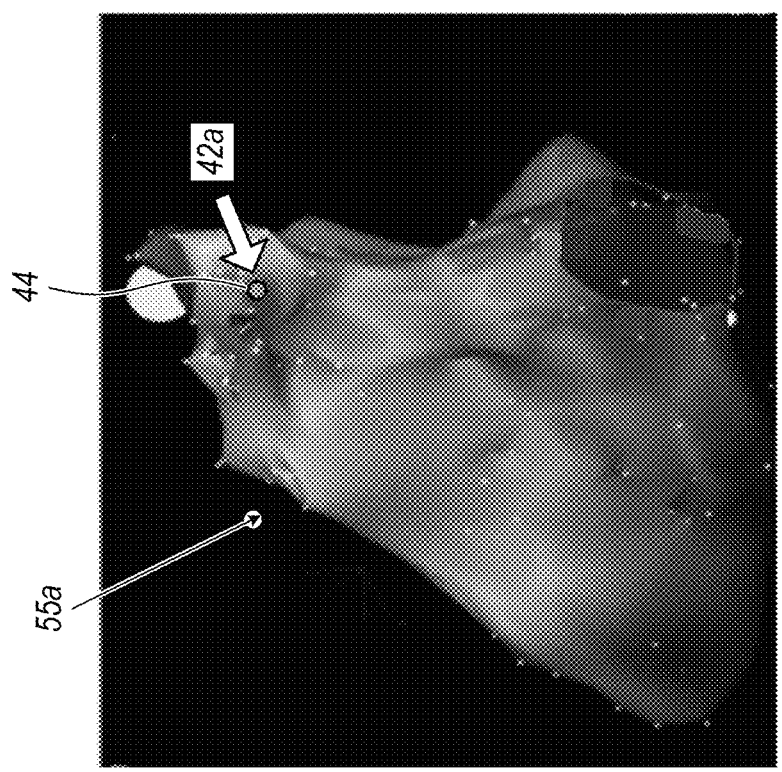

Reference is now made to FIG. 2, which is a schematic illustration of two electroanatomical maps, in accordance with some examples of the present disclosure.

FIG. 2 depicts an arrhythmic electroanatomical map 55a, which is an instance of map 55 (FIG. 1). Arrhythmic electroanatomical map 55a maps a portion of heart 26 (FIG. 1) while the heart experiences an arrhythmia, including, for example, premature ventricular contraction (PVC). Typically, map 55a is colored and/or otherwise annotated so as to indicate respective local activation times (LATs), activation voltages, and/or values of any other electrical property at various points on the tissue. Map 55a may represent the portion of the heart at the start of the QRS complex, the start of the T-wave, the start of the P-wave, or any other suitable phase of the cardiac cycle.

Processor 39 (FIG. 1) is configured to obtain map 55a. For example, the processor may construct the map as described above with reference to FIG. 1. Alternatively, for example, the processor may load the map from memory 37 (FIG. 1) or receive the map over a computer network.

FIG. 2 further shows a marker 44 marking a particular portion 42a of map 55a. Portion 42a, which may have any shape and area, may correspond to the focal point of the arrhythmia or to any other anatomical portion of interest.

In some examples, the processor receives an input, from a user, indicating portion 42a. For example, portion 42a may be marked by physician 30 (FIG. 1) while map 55a is displayed on display 27. Alternatively, portion 42a may be identified automatically by the processor. (It is noted that marker 44 need not necessarily be displayed by the processor.)

FIG. 2 further shows a rhythmic electroanatomical map 55r, which is also an instance of map 55 (FIG. 1). Rhythmic electroanatomical map 55r maps the same portion of the heart as does map 55a, in the same coordinate system and at the same phase of the cardiac cycle, while the heart is in sinus rhythm. Map 55r differs from map 55a due to differences in morphology and electrical conduction between the arrhythmic and rhythmic states of the heart.

Processor 39 (FIG. 1) is configured to obtain map 55r, as described above for map 55a. For example, the processor may construct both maps in parallel. In particular, mapping-and-ablation probe 22 (FIG. 1) may acquire intracardiac signals over one or more periods of sinus rhythm and one or more periods of arrhythmia. For each intracardiac signal received from the probe, the processor may check the subject's ECG. If the ECG indicates that the heart is in sinus rhythm, the processor may assign the signal (with its associated location) to map 55r; otherwise, the processor may assign the signal to map 55a.

In some examples, as further described below with reference to FIG. 3, the processor is configured to identify a portion 42r of map 55r, which corresponds to portion 42a of map 55a by virtue of representing the same anatomical portion. Subsequently to identifying portion 42r, the processor may display map 55r with marker 44 overlaying portion 42r.

Figure 3:
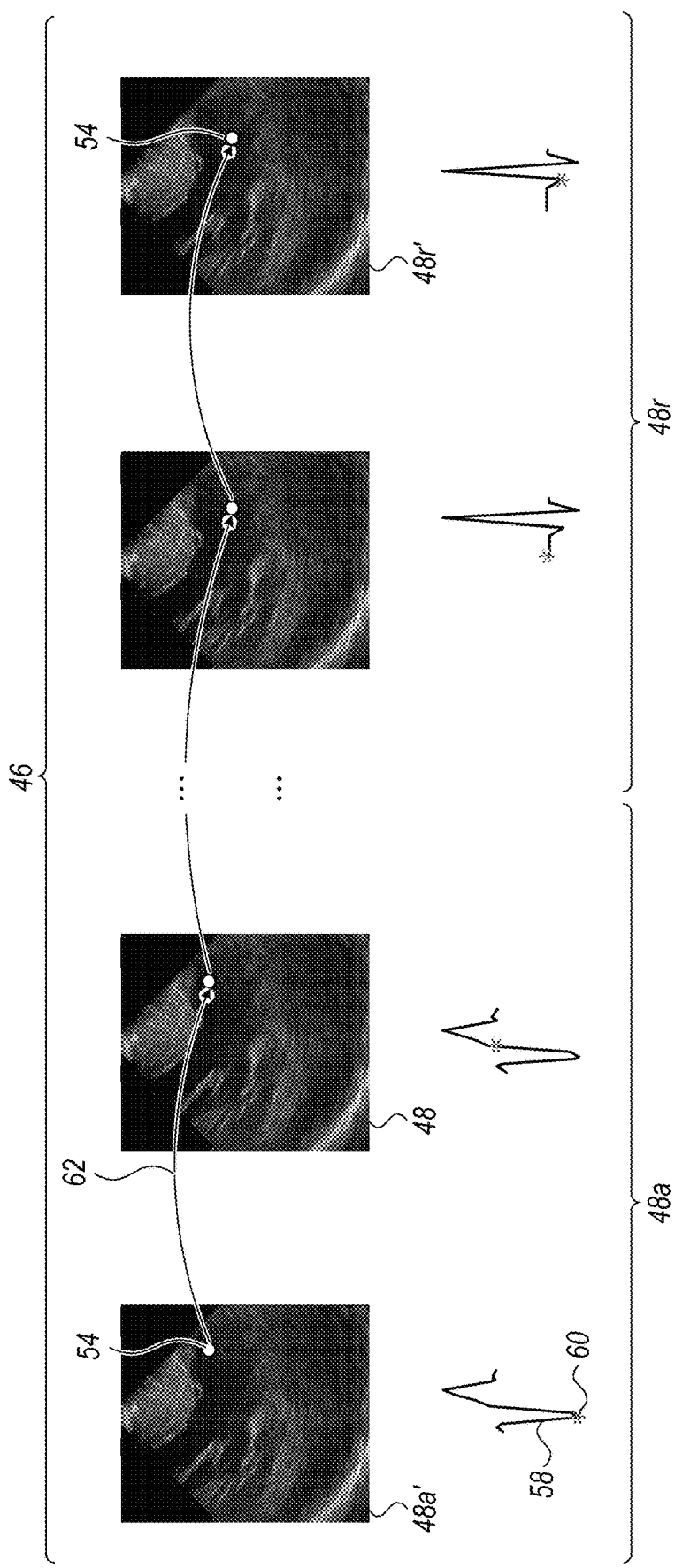
FIG. 3 is a schematic illustration of a technique for tracking an anatomical portion, in accordance with some examples of the present disclosure.

Reference is now further made to FIG. 3, which is a schematic illustration of a technique for tracking an anatomical portion, in accordance with some examples of the present disclosure.

Mapping processor 39 (FIG. 1) is configured to obtain a sequence 46 of images 48 of the heart acquired by US probe 21 (FIG. 1). For example, the mapping processor may receive the sequence from ultrasound processor 41, load the sequence from memory 37, or receive the sequence from a remote computer via a computer network.

Sequence 46 includes one or more arrhythmic images 48a acquired while the heart experiences the arrhythmia, and one or more rhythmic images 48r acquired while the heart is in sinus rhythm. Arrhythmic images 48a may be acquired before or after rhythmic images 48r. In other words, during the acquisition of the sequence, the heart may transition from arrhythmia to sinus rhythm or from sinus rhythm to arrhythmia. Typically, images 48 (which may also be referred to as "frames") in sequence 46 are acquired at a rate of at least 30 frames per second (fps), such as 30-60 fps. At least some of images 48 may be acquired with different respective fields of view.

For each image 48 shown in FIG. 3, FIG. 3 further shows a portion of the ECG waveform 58 of the subject, with a marker 60 indicating the phase in the cardiac cycle at which the image was acquired. By way of example, the portion of ECG waveform 58 shown in FIG. 3 includes the QRS complex. While the heart is arrhythmic, the QRS complex may be abnormal, as depicted in FIG. 3.

In some examples, the raw data used to construct map 55a and the raw data used to construct arrhythmic images 48a are acquired during the same episode of the arrhythmia. For example, US probe 21 and mapping-and-ablation probe 22 (FIG. 1) may be situated simultaneously in the subject's heart while the episode occurs. In other examples, the raw data used to construct map 55a and the raw data used to construct arrhythmic images 48a are acquired during different respective episodes of the arrhythmia.

As described above with reference to FIG. 1, US probe 21 and mapping-and-ablation probe 22 are tracked using the same tracking system, or alternatively, the same probe is used for both mapping and ultrasound. In either case, the signal output by tracking sensor 52 (FIG. 1) indicates the location and orientation of the US probe in the coordinate system of maps 55a and 55r; in other words, images 48 are registered to maps 55a and 55r. Hence, based on the tracking signal, the mapping processor identifies, in an arrhythmic image 48a', the anatomical portion 54 represented by portion 42a of map 55a.

Typically, arrhythmic image 48a' is acquired at approximately the same phase of the cardiac cycle as the phase represented by map 55a, and is closer to the rhythmic images than any other arrhythmic image acquired at such a phase. For example, for cases in which the arrhythmic images precede the rhythmic images, the mapping processor may identify arrhythmic image 48a' by, beginning with the last arrhythmic image, moving backward through sequence 46 until the cardiac phase is within a predefined threshold of the phase represented by map 55*a*. For cases in which the arrhythmic images follow the rhythmic images, the mapping processor may, beginning with the first arrhythmic image, move forward through sequence 46 until the cardiac phase is within the predefined threshold of the phase represented by map 55*a*.

Subsequently to identifying anatomical portion 54 in arrhythmic image 48*a*', the mapping processor tracks the anatomical portion across the sequence of images, as indicated in FIG. 3 by a tracking indicator 62. If rhythmic images 48*r* follow arrhythmic images 48*a*, the processor tracks the anatomical portion forward through the sequence; otherwise, the processor tracks the anatomical portion backward through the sequence. In either case, by tracking anatomical portion 54, the processor identifies the anatomical portion in at least one of the rhythmic images. In particular, the processor may stop the tracking upon identifying the anatomical portion in a rhythmic image 48*r*', which is acquired at approximately the same phase as arrhythmic image 48*a*' and is closer to the arrhythmic images than any other rhythmic image acquired at such a phase.

Typically, the mapping processor tracks the anatomical portion using a speckle-tracking technique, such as the technique described in Bohs, Laurence N., and Gregg E. Trahey, "A novel method for angle independent ultrasonic imaging of blood flow and tissue motion," IEEE Transactions on biomedical engineering 38.3 (1991): 280-286, whose disclosure is incorporated herein by reference.

Subsequently, the mapping processor displays an output (e.g., on display 27 (FIG. 1)) in response to identifying anatomical portion 54 in at least one of the rhythmic images.

In some examples, the output includes rhythmic image 48*r*', and/or any other rhythmic image in which the anatomical portion was identified, with an overlaid marker (such as the marker shown in FIG. 3) marking the anatomical portion.

Alternatively or additionally, in response to identifying anatomical portion 54 in rhythmic image 48*r*' and based on the signal output by the tracking sensor, the processor may identify portion 42*r* of map 55*r*, which corresponds to portion 42*a* of map 55*a* by virtue of representing anatomical portion 54. In other words, by virtue of rhythmic image 48*r*' being registered to, and at approximately the same cardiac phase as, map 55*r*, the processor may identify portion 42*r*. Subsequently, the processor may mark portion 42*r*, as described above with reference to FIG. 2.

Constructing a Hybrid Electroanatomical Map

In other examples, the mapping processor constructs and displays a hybrid electroanatomical map, in which an anatomical map representing the portion of the heart during sinus rhythm is annotated so as to indicate respective values of an electrical property, such as LAT, at multiple anatomical portions during the arrhythmia. The hybrid map may then be marked so as to show the location of a focal point or any other point of interest.

In particular, the processor may perform the tracking described above with reference to FIGS. 2-3 for multiple anatomical portions represented by different respective representative portions of the arrhythmic electroanatomical map. If a single sequence does not show the entire portion of the heart, the tracking may be performed over multiple sequences, i.e., at least one of the anatomical portions may be tracked over a different sequence than another one of the anatomical portions.

Based on the tracking, the processor may identify, for each representative portion of the arrhythmic electroanatomical map, the corresponding portion of an anatomical map representing the portion of the heart while the heart is in sinus rhythm. The processor may then associate, with each identified portion of the anatomical map, the value(s) of the electrical property at the corresponding portion of the arrhythmic map.

Figure 4:
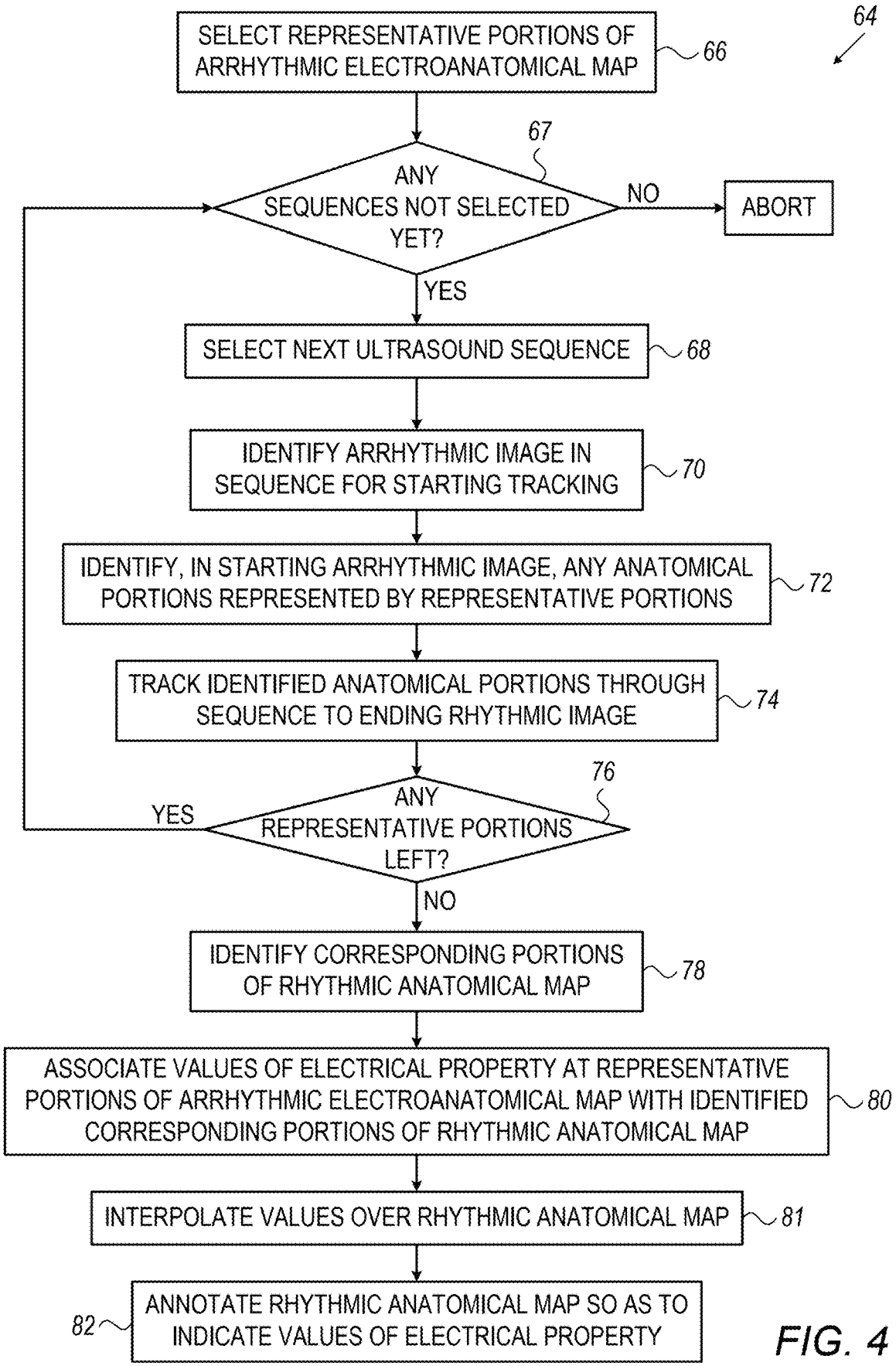
FIG. 4 is a flow diagram for an algorithm for constructing a hybrid electroanatomical map, in accordance with some examples of the present disclosure.

For further details, reference is now made to FIG. 4, which is a flow diagram for an algorithm 64 for constructing a hybrid electroanatomical map, in accordance with some examples of the present disclosure.

Algorithm 64 begins with a portion-selecting step 66, at which the processor selects multiple representative portions of the arrhythmic electroanatomical map. For example, the processor may select every portion of the map associated with an electrical-property value acquired by one of electrodes 25 (FIG. 1), as opposed to portions of the map associated with interpolated values. Alternatively, for example, the processor may select every portion of the map, including those associated with interpolated values.

Following portion-selecting step 66, the processor checks, at a checking step 67, whether there is at least one ultrasound sequence that includes both rhythmic and arrhythmic images (as described above with reference to FIG. 3) and was not yet selected. If not, the processor aborts the construction of the hybrid electroanatomical map. Otherwise, the processor, at a sequence-selecting step 68, selects an ultrasound sequence that was not yet selected.

Next, at an image-identifying step 70, the processor identifies an arrhythmic image in the selected sequence that is suitable for starting the tracking. Example criteria for identifying such an image are described above with reference to arrhythmic image 48*a*' of FIG. 3.

Subsequently, the processor, at an anatomical-portion-identifying step 72, identifies, in the identified "starting" arrhythmic image, any anatomical portions represented by respective representative portions of the arrhythmic map. The processor then tracks the identified anatomical portions through the sequence, at a tracking step 74, until reaching an "ending" rhythmic image, which may be identified as described above with reference to rhythmic image 48*r*' of FIG. 3.

Next, the processor checks, at a checking step 76, whether any of the representative portions have not yet been accounted for. If yes, the processor returns to checking step 67. Otherwise, the processor, at an identifying step 78, identifies the portions of a rhythmic anatomical map that correspond to the tracked anatomical portions. Subsequently, the processor, at an associating step 80, associates values of an electrical property, such as LAT, at the representative portions of the arrhythmic map with the identified corresponding portions of the anatomical map, respectively.

Next, at an interpolating step 81, the processor interpolates the values of the electrical property over the rhythmic anatomical map. (In the event that the representative portions include the entire arrhythmic map, there may be relatively little, or no, interpolation required.) Finally, at an annotating step 82, the processor annotates the rhythmic anatomical map so as to indicate the values of the electrical property.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system (20) includes a display (27) and one or more processors (39, 41) configured to cooperatively carry out a process. The process includes obtaining an electroanatomical map (55a), which maps a portion of a heart (26) of a subject (28) while the heart experiences an arrhythmia. The process further includes obtaining a sequence (46) of images (48) of the heart acquired by an ultrasonic probe (21), the sequence including one or more arrhythmic images (48a) acquired while the heart experiences the arrhythmia and one or more rhythmic images (48r) acquired while the heart is in sinus rhythm, the ultrasonic probe including a sensor (52) that outputs, during the acquisition of the sequence of images, a signal indicating a location and an orientation of the probe in a coordinate system of the electroanatomical map. The processor further includes, based on the signal, identifying, in one of the arrhythmic images, an anatomical portion (54) represented by a particular portion (42a) of the electroanatomical map. The process further includes, by tracking the anatomical portion through the sequence of images, identifying the anatomical portion in at least one of the rhythmic images, and displaying an output on the display (27) in response to identifying the anatomical portion in the at least one of the rhythmic images.

Example 2

The system (20) according to Example 1, wherein the output includes the at least one of the rhythmic images (48r) with an overlaid marker marking the anatomical portion (54).

Example 3

The system (20) according to Example 1,
wherein the electroanatomical map is an arrhythmic electroanatomical map (55a),
wherein the process further includes obtaining a rhythmic electroanatomical map (55r), which maps the portion of the heart (26), in the coordinate system, while the heart is in sinus rhythm, and
wherein displaying the output includes:
in response to identifying the anatomical portion (54) in the at least one of the rhythmic images (48r) and based on the signal, identifying a portion (42r) of the rhythmic electroanatomical map corresponding to the particular portion (42a) of the arrhythmic electroanatomical map by virtue of representing the anatomical portion (54), and
displaying the rhythmic electroanatomical map with an overlaid marker (44) at the identified portion of the rhythmic electroanatomical map.

Example 4

The system (20) according to Example 1,
wherein the electroanatomical map is an arrhythmic electroanatomical map (55a),
wherein the particular portion (42a) is one of multiple representative portions of the arrhythmic electroanatomical map,
wherein the anatomical portion (54) is one of multiple anatomical portions represented by the representative portions, respectively,
wherein the sequence (46) is one of one or more sequences,
wherein the process includes tracking each of the anatomical portions through a respective one of the sequences, and
wherein displaying the output includes:
constructing a hybrid electroanatomical map, in which an anatomical map representing the portion of the heart during sinus rhythm is annotated so as to indicate respective values of an electrical property at the anatomical portions during the arrhythmia, and
displaying the hybrid electroanatomical map.

Example 5

The system (20) according to any one of Examples 1-4, wherein the anatomical portion (54) includes a focal point of the arrhythmia.

Example 6

The system (20) according to any one of Examples 1-5, wherein the arrhythmia includes premature ventricular contraction (PVC).

Example 7

The system (20) according to any one of Examples 1-6, wherein the arrhythmic images (48a) are acquired before the rhythmic images (48r).

Example 8

The system (20) according to any one of Examples 1-6, wherein the arrhythmic images (48a) are acquired after the rhythmic images (48r).

Example 9

The system (20) according to any one of Examples 1-8, wherein the process further includes receiving an input, from a user, indicating the particular portion (42a) of the electroanatomical map (55a).

Example 10

A method includes obtaining an electroanatomical map (55a), which maps a portion of a heart (26) of a subject (28) while the heart experiences an arrhythmia. The method further includes obtaining a sequence (46) of images (48) of the heart acquired by an ultrasonic probe (21), the sequence including one or more arrhythmic images (48a) acquired while the heart experiences the arrhythmia and one or more rhythmic images (48r) acquired while the heart is in sinus rhythm, the ultrasonic probe including a sensor (52) that outputs, during the acquisition of the sequence of images, a signal indicating a location and an orientation of the probe in a coordinate system of the electroanatomical map. The method further includes, based on the signal, identifying, in one of the arrhythmic images, an anatomical portion (54) represented by a particular portion (42a) of the electroanatomical map. The method further includes, by tracking the anatomical portion through the sequence of images, identifying the anatomical portion in at least one of the rhythmic images, and displaying an output in response to identifying the anatomical portion in the at least one of the rhythmic images.

Example 11

The method according to Example 10, wherein the output includes the at least one of the rhythmic images (48r) with an overlaid marker marking the anatomical portion (54).

Example 12

The method according to Example 10,
wherein the electroanatomical map is an arrhythmic electroanatomical map (55a),
wherein the method further includes obtaining a rhythmic electroanatomical map (55r), which maps the portion of the heart (26), in the coordinate system, while the heart is in sinus rhythm, and
wherein displaying the output includes:
  in response to identifying the anatomical portion (54) in the at least one of the rhythmic images (48r) and based on the signal, identifying a portion (42r) of the rhythmic electroanatomical map corresponding to the particular portion (42a) of the arrhythmic electroanatomical map by virtue of representing the anatomical portion (54); and
  displaying the rhythmic electroanatomical map with an overlaid marker (44) at the identified portion of the rhythmic electroanatomical map.

Example 13

The method according to Example 10,
wherein the electroanatomical map is an arrhythmic electroanatomical map (55a),
wherein the particular portion (42a) is one of multiple representative portions of the arrhythmic electroanatomical map,
wherein the anatomical portion (54) is one of multiple anatomical portions represented by the representative portions, respectively,
wherein the sequence (46) is one of one or more sequences,
wherein the method includes tracking each of the anatomical portions through a respective one of the sequences, and
wherein displaying the output includes:
  constructing a hybrid electroanatomical map, in which an anatomical map representing the portion of the heart during sinus rhythm is annotated so as to indicate respective values of an electrical property at the anatomical portions during the arrhythmia; and
  displaying the hybrid electroanatomical map.

Example 14

The method according to any one of Examples 10-13, wherein the anatomical portion (54) includes a focal point of the arrhythmia.

Example 15

The method according to any one of Examples 10-14, wherein the arrhythmia includes premature ventricular contraction (PVC).

Example 16

The method according to any one of Examples 10-15, wherein the arrhythmic images are acquired before the rhythmic images.

Example 17

The method according to any one of Examples 10-15, wherein the arrhythmic images are acquired after the rhythmic images.

Example 18

The method according to any one of Examples 10-17, further including receiving an input, from a user, indicating the particular portion of the electroanatomical map.

Example 19

A computer software product includes a tangible non-transitory computer-readable medium in which program instructions are stored. The instructions, when read by a processor (39, 41), cause the processor to obtain an electroanatomical map (55a), which maps a portion of a heart (26) of a subject (28) while the heart experiences an arrhythmia. The instructions further cause the processor to obtain a sequence (46) of images (48) of the heart acquired by an ultrasonic probe (21), the sequence including one or more arrhythmic images (48a) acquired while the heart experiences the arrhythmia and one or more rhythmic images (48r) acquired while the heart is in sinus rhythm, the ultrasonic probe including a sensor (52) that outputs, during the acquisition of the sequence of images, a signal indicating a location and an orientation of the probe in a coordinate system of the electroanatomical map. The instructions further cause the processor to identify in one of the arrhythmic images, based on the signal, an anatomical portion (54) represented by a particular portion (42a) of the electroanatomical map. The instructions further cause the processor to track the anatomical portion through the sequence of images so as to identify the anatomical portion in at least one of the rhythmic images, and to display an output in response to identifying the anatomical portion in the at least one of the rhythmic images.

Example 20

The computer software product according to Example 19,
wherein the electroanatomical map is an arrhythmic electroanatomical map,
wherein the instructions further cause the processor to obtain a rhythmic electroanatomical map, which maps the portion of the heart, in the coordinate system, while the heart is in sinus rhythm, and wherein the instructions cause the processor to display the output by:

in response to identifying the anatomical portion in the at least one of the rhythmic images and based on the signal, identifying a portion of the rhythmic electroanatomical map corresponding to the portion of the arrhythmic electroanatomical map by virtue of representing the anatomical portion, and displaying the rhythmic electroanatomical map with an overlaid marker at the identified portion of the rhythmic electroanatomical map.

It will be appreciated by persons skilled in the art that the present disclosure is not limited to what has been particularly shown and described hereinabove. Rather, the scope of the present disclosure includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a display; and
one or more processors configured to cooperatively carry out a process including:
obtaining an electroanatomical map, which maps a portion of a heart of a subject while the heart experiences an arrhythmia,
obtaining a sequence of images of the heart acquired by an ultrasonic probe, the sequence including one or more arrhythmic images acquired while the heart experiences the arrhythmia and one or more rhythmic images acquired while the heart is in sinus rhythm,
the ultrasonic probe including a sensor that outputs, during the acquisition of the sequence of images, a signal indicating a location and an orientation of the probe in a coordinate system of the electroanatomical map,
based on the signal, identifying, in one of the arrhythmic images, an anatomical portion represented by a particular portion of the electroanatomical map, the anatomical portion being a focal point of the arrhythmia,
by tracking the anatomical portion forward or backward through the acquired sequence of images, identifying the anatomical portion in at least one of the rhythmic images, and
displaying an output on the display in response to identifying the anatomical portion in the at least one of the rhythmic images.

2. System according to claim 1, wherein the output includes the at least one of the rhythmic images with an overlaid marker marking the anatomical portion.

3. The system according to claim 1,
wherein the electroanatomical map is an arrhythmic electroanatomical map,
wherein the process further includes obtaining a rhythmic electroanatomical map, which maps the portion of the heart, in the coordinate system, while the heart is in sinus rhythm, and
wherein displaying the output includes:
in response to identifying the anatomical portion in the at least one of the rhythmic images and based on the signal, identifying a portion of the rhythmic electroanatomical map corresponding to the particular portion of the arrhythmic electroanatomical map by virtue of representing the anatomical portion, and
displaying the rhythmic electroanatomical map with an overlaid marker at the identified portion of the rhythmic electroanatomical map.

4. The system according to claim 1, wherein the electroanatomical map is an arrhythmic electroanatomical map,
wherein the particular portion is one of multiple representative portions of the arrhythmic electroanatomical map,
wherein the anatomical portion is one of multiple anatomical portions represented by the representative portions, respectively,
wherein the sequence is one of one or more sequences,
wherein the process includes tracking each of the anatomical portions through a respective one of the sequences, and
wherein displaying the output includes:
constructing a hybrid electroanatomical map, in which an anatomical map representing the portion of the heart during sinus rhythm is annotated so as to indicate respective values of an electrical property at the anatomical portions during the arrhythmia, and
displaying the hybrid electroanatomical map.

5. The system according to claim 1, wherein the anatomical portion includes a focal point of the arrhythmia.

6. The system according to claim 1, wherein the arrhythmia includes premature ventricular contraction (PVC).

7. The system according to claim 1, wherein the arrhythmic images are acquired before the rhythmic images.

8. The system according to claim 1, wherein the arrhythmic images are acquired after the rhythmic images.

9. The system according to claim 1, wherein the process further includes receiving an input, from a user, indicating the particular portion of the electroanatomical map.

10. A method, comprising:
obtaining an electroanatomical map, which maps a portion of a heart of a subject while the heart experiences an arrhythmia;
obtaining a sequence of images of the heart acquired by an ultrasonic probe, the sequence including one or more arrhythmic images acquired while the heart experiences the arrhythmia and one or more rhythmic images acquired while the heart is in sinus rhythm,
the ultrasonic probe including a sensor that outputs, during the acquisition of the sequence of images, a signal indicating a location and an orientation of the probe in a coordinate system of the electroanatomical map;
based on the signal, identifying, in one of the arrhythmic images, an anatomical portion represented by a particular portion of the electroanatomical map the anatomical portion being a focal point of the arrhythmia;
by tracking the anatomical portion forward or backward through the acquired sequence of images, identifying the anatomical portion in at least one of the rhythmic images; and displaying an output in response to identifying the anatomical portion in the at least one of the rhythmic images.

11. The method according to claim 10, wherein the output includes the at least one of the rhythmic images with an overlaid marker marking the anatomical portion.

12. The method according to claim 10,
wherein the electroanatomical map is an arrhythmic electroanatomical map,
wherein the method further comprises obtaining a rhythmic electroanatomical map, which maps the portion of the heart, in the coordinate system, while the heart is in sinus rhythm, and
wherein displaying the output comprises:
 in response to identifying the anatomical portion in the at least one of the rhythmic images and based on the signal, identifying a portion of the rhythmic electroanatomical map corresponding to the particular portion of the arrhythmic electroanatomical map by virtue of representing the anatomical portion; and
 displaying the rhythmic electroanatomical map with an overlaid marker at the identified portion of the rhythmic electroanatomical map.

13. The method according to claim 10,
wherein the electroanatomical map is an arrhythmic electroanatomical map,
wherein the particular portion is one of multiple representative portions of the arrhythmic electroanatomical map,
wherein the anatomical portion is one of multiple anatomical portions represented by the representative portions, respectively,
wherein the sequence is one of one or more sequences,
wherein the method comprises tracking each of the anatomical portions through a respective one of the sequences, and
wherein displaying the output comprises:
 constructing a hybrid electroanatomical map, in which an anatomical map representing the portion of the heart during sinus rhythm is annotated so as to indicate respective values of an electrical property at the anatomical portions during the arrhythmia; and
 displaying the hybrid electroanatomical map.

14. The method according to claim 10, wherein the anatomical portion includes a focal point of the arrhythmia.

15. The method according to claim 10, wherein the arrhythmia includes premature ventricular contraction (PVC).

16. The method according to claim 10, wherein the arrhythmic images are acquired before the rhythmic images.

17. The method according to claim 10, wherein the arrhythmic images are acquired after the rhythmic images.

18. The method according to claim 10, further comprising receiving an input, from a user, indicating the particular portion of the electroanatomical map.

19. A computer software product comprising a tangible non-transitory computer-readable medium in which program instructions are stored, which instructions, when read by a processor, cause the processor to:
 obtain an electroanatomical map, which maps a portion of a heart of a subject while the heart experiences an arrhythmia,
 obtain a sequence of images of the heart acquired by an ultrasonic probe, the sequence including one or more arrhythmic images acquired while the heart experiences the arrhythmia and one or more rhythmic images acquired while the heart is in sinus rhythm,
  the ultrasonic probe including a sensor that outputs, during the acquisition of the sequence of images, a signal indicating a location and an orientation of the probe in a coordinate system of the electroanatomical map,
 based on the signal, identify, in one of the arrhythmic images, an anatomical portion represented by a particular portion of the electroanatomical map,
 by tracking the anatomical portion through the sequence of images, identify the anatomical portion in at least one of the rhythmic images, and
 display an output in response to identifying the anatomical portion in the at least one of the rhythmic images.

20. The computer software product according to claim 19,
wherein the electroanatomical map is an arrhythmic electroanatomical map,
wherein the instructions further cause the processor to obtain a rhythmic electroanatomical map, which maps the portion of the heart, in the coordinate system, while the heart is in sinus rhythm, and
wherein the instructions cause the processor to display the output by:
 in response to identifying the anatomical portion in the at least one of the rhythmic images and based on the signal, identifying a portion of the rhythmic electroanatomical map corresponding to the portion of the arrhythmic electroanatomical map by virtue of representing the anatomical portion, and
 displaying the rhythmic electroanatomical map with an overlaid marker at the identified portion of the rhythmic electroanatomical map.

* * * * *